US006718656B2

(12) United States Patent
Houser et al.

(10) Patent No.: US 6,718,656 B2
(45) Date of Patent: Apr. 13, 2004

(54) SHOES AND BRACES WITH SUPERELASTIC SUPPORTS

(76) Inventors: Russell A. Houser, 1787 Verdite St., Livermore, CA (US) 94550; James G. Whayne, 137 New Castle Dr., Chapel Hill, NC (US) 27514

( * ) Notice: Subject to any disclaimer, the term of this patent is extended or adjusted under 35 U.S.C. 154(b) by 0 days.

(21) Appl. No.: 09/898,577

(22) Filed: Jul. 3, 2001

(65) Prior Publication Data

US 2002/0038522 A1 Apr. 4, 2002

Related U.S. Application Data

(60) Provisional application No. 60/216,045, filed on Jul. 5, 2000.

(51) Int. Cl.[7] ............................. A43B 7/14; A43B 7/20; A61F 13/00
(52) U.S. Cl. ..................... 36/88; 36/89; 602/5; 602/26; 602/27; 602/62; 602/63; 602/65
(58) Field of Search ................................ 36/27, 28, 88, 36/89; 602/5, 12, 26, 27, 62, 65, 63

(56) References Cited

U.S. PATENT DOCUMENTS

| | | | | | |
|---|---|---|---|---|---|
| 291,490 | A | * | 1/1884 | Buch ............................... 36/28 |
| 4,316,335 | A | * | 2/1982 | Giese et al. .................... 36/129 |
| 4,616,431 | A | * | 10/1986 | Dassler ........................... 36/28 |
| 5,007,417 | A | * | 4/1991 | Bender ........................... 36/89 |
| 5,125,171 | A | * | 6/1992 | Stewart ......................... 36/114 |
| 5,152,082 | A | * | 10/1992 | Culpepper .................... 36/114 |
| 5,261,871 | A | * | 11/1993 | Greenfield |
| 5,337,492 | A | * | 8/1994 | Anderie et al. ............... 36/114 |
| 5,353,523 | A | * | 10/1994 | Kilgore et al. ................. 36/28 |
| 5,493,791 | A | * | 2/1996 | Kramer .......................... 36/28 |
| 5,544,431 | A | * | 8/1996 | Dixon ............................ 36/27 |
| 5,678,327 | A | * | 10/1997 | Halberstadt .................... 36/27 |
| 5,713,836 | A | * | 2/1998 | O'keefe ......................... 602/5 |
| 5,743,028 | A | * | 4/1998 | Lombardino ................... 36/27 |
| 5,775,008 | A | * | 7/1998 | Bussell et al. ................. 36/89 |
| 5,778,563 | A | * | 7/1998 | Ahlbaumer ................... 36/140 |
| 6,029,374 | A | * | 2/2000 | Herr et al. ..................... 36/27 |
| 6,041,521 | A | * | 3/2000 | Wong ............................ 36/28 |
| 6,055,747 | A | * | 5/2000 | Lombardino ................... 36/27 |
| 6,170,175 | B1 | * | 1/2001 | Funk ............................ 36/115 |
| 6,200,685 | B1 | * | 3/2001 | Davidson ................. 428/472.1 |
| 6,219,940 | B1 | * | 4/2001 | Kita |
| 6,371,464 | B1 | * | 4/2002 | Porche et al. ............. 267/166.1 |
| 6,422,010 | B1 | * | 7/2002 | Julien ........................... 60/527 |

FOREIGN PATENT DOCUMENTS

WO         01/41595        *  6/2001

OTHER PUBLICATIONS

"Application Examples of Shape Memory and Superelastic Alloys", Shape Memory Applicatios, Inc. 1999.*
NiTi Smart Sheet, "Making Shape Memory Springs", Smart Memory Applications, Inc. 1999.*

* cited by examiner

*Primary Examiner*—M. D. Patterson

(57) ABSTRACT

Described are shoes, orthodic appliances, and anatomic braces containing superelastic support members for enhanced performance. The superelastic supports provide dynamic response to deflection. As such, the superelastic supports incorporated in the soles of shoes enhance walking, running, jumping, kicking, or other motion involving the foot. The superelastic supports may be incorporated in the body of shoes to reinforce the ankle joint. The embodiments of the invention also provide superelastic supports in braces to reinforce or stabilize the knees, ankles, elbows, wrists, shoulders, back, neck, hips, or other anatomy commonly associated with a degree of twisting, rotation, bending, or other desired motion. The braces also intensify the motion of anatomic structures, apply a specific resistance at the joint to strengthen the muscles during training or rehabilitation, and/or immobilize or stabilize joints, bones, or other anatomic structures during healing of an injury.

9 Claims, 12 Drawing Sheets

SHOES AND BRACES WITH SUPERELASTIC SUPPORTS

CROSS REFERENCE TO RELATED APPLICATION

This application claims priority to provisional U.S. patent application Ser. No. 60/216,045, entitled "Shoes and Braces with Superelastic Supports", filed Jul. 5, 2000, the entirety of which is hereby incorporated by reference.

FIELD OF THE INVENTION

This invention relates to devices for enhancing the performance of shoes or braces. More particularly, the invention relates to supports that are incorporated in the soles of shoes to improve the vertical jump, the lateral agility, and the running stride of the shoe wearer. The supports also provide cushions for the heel and the ball of the foot to prevent injury occurring from pounding the foot against a hard surface. In addition, the supports facilitate walking by providing an upward force in response to downward deflection mimicking the natural motion of the foot and easing the stress of walking on the foot. The supports also correct congenital defects such as pronation and supenation by urging the foot into the correct position while walking or exercising.

The embodiments of the invention also provide supports to reinforce the joints and prevent unwanted twisting, rolling, rotating, or bending. The supports may be incorporated in shoes to integrally provide reinforcement of the ankles or may be used in separate ankle braces to prevent unwanted or excess rolling, twisting, or bending of the ankle. Alternatively, the supports may be inserted into the ankle or body regions of shoes to provide additional reinforcement to the foot without being integrally encapsulated into the shoe; as such these supports function as orthodic appliances. The supports may also be used in knee, wrist, shoulder, or elbow braces to prevent unwanted twisting or bending at these joints. The supports may also be incorporated into rib, or other bone, guards to reinforce the ribs, or other bone, and distribute the stress applied to the ribs, or other bone. This prevents extremely concentrated force, which potentially causes fracture or other injury to the rib, tibia, or other bone.

DESCRIPTION OF THE RELATED ART

Current techniques for providing a cushion or spring involve using pockets of air incorporated in the shoe sole. Such pockets are intended to decrease and distribute the impact upon the foot when landing on a hard surface but do not exert an opposing force on the foot capable of aiding the shoe wearer in walking, running, or jumping. In addition, air pockets must typically be inflated to high pressures so the pockets have enough rigidity to withstand the weight of the shoe wearer without collapsing; as such, the pockets do not provide enough compression to cushion the foot. A need thus exists for shoe supports that are capable of being deflected a predetermined amount in response to an external force and exerting an opposing force in response to the deflection.

SUMMARY OF THE INVENTION

The embodiments of the present invention provide shoes that contain superelastic supports that elastically return towards their baseline configuration when deflected by an external force. As such these superelastic supports may be utilized in the soles of shoes to produce an opposing force once deflected and enhance walking, running, moving side-to-side, or jumping. The supports also correct abnormalities such as pronation and supenation by directing the foot into the desired position for walking or exercising.

The embodiments of the present invention also provide shoes, inserts, or braces that contain superelastic supports to reinforce the ankle, knee, elbow, ribs, shin, other bone, or other joint by preventing unwanted or excess twisting, rotating, localized stressing, or bending at the joint or bone. The embodiments also provide braces incorporating superelastic supports that reinforce or stabilize anatomic structures thereby treating sprains, fractures, or other injury. In addition, the embodiments provide braces to reinforce or apply continuous force on the sternum or ribs and ensure rapid and evenly distributed healing of the sternum or ribs after open heart surgery involving a median sternotomy, thoracotomy, or thoracostomy.

The above described and many further features and advantages of the present invention will be elaborated in the following detailed description and accompanying drawings.

BRIEF DESCRIPTION OF THE DRAWINGS

FIGS. 1a and b show top views of the soles of a left shoe and a right shoe, respectively, incorporating superelastic support members;

FIG. 9b shows the flattened perspective of the superelastic support member in FIG. 9a;

FIG. 10b shows the flattened perspective of the memory elastic support member in FIG. 10a;

DETAILED DESCRIPTION OF THE INVENTION

The following is a detailed description of the presently best known modes of carrying out the inventions. This detailed description is not to be taken in a limiting sense, but is made merely for the purpose of illustrating the general principles of the inventions.

This specification discloses a number of embodiments, mainly in the context of reinforcement, abnormality correction, and performance enhancement for shoes, joint braces, and bone scaffolds. Nevertheless, it should be appreciated that the structures are applicable for use in other indications involving devices that are used to exert continuous force against anatomic structures once positioned, and/or are capable of exerting a desired force in response to an externally induced deflection.

The embodiments of the invention provide support members fabricated from superelastic (pseudoelastic) shape memory alloys. These superelastic support members elastically deform upon exposure to an external force and return towards their preformed shape upon reduction or removal of the external force. The superelastic support members exhibit stress-induced martensite characteristics in that they transform from the preshaped austenite form to the more soft and ductile martensite form upon application of stress and transform back toward the more strong and hard austenite form once the stress is released. Superelastic shape memory alloys also enable straining the material numerous times without plastically deforming the material. Superelastic shape memory alloys are also light in weight, and exhibit excellent tensile strengths such that they may be inserted in the soles of shoes, ankle regions of shoes, body of shoes, joint braces, or other devices without dramatically increasing the weight of the device or making the device extremely thick and bulky. These characteristics highlight their utility in providing support to the soles of shoes because they withstand continuous and frequent deflections without plastically deforming or observing fatigue failures. These support members may be elastically deflected into small radii of curvature and return towards their preformed configuration once the external force causing the deflection is removed. Other known metal, alloy, and thermoplastic materials plastically deform when deflected into similar radii of curvature, using comparable strains and are unable to return towards their original configuration. As such, superelastic support members permit deflections into smaller radii of curvature than other metals, alloys, and polymers resulting in larger strains, and they are capable of exerting substantial force when deflected.

Superelastic support members are preferably fabricated from shape memory alloys (e.g. nickel titanium) demonstrating stress-induced martensite at ambient temperature. The composition of the shape memory alloy is preferably chosen to produce martensite transformation temperatures (Mf and Ms) and austenite temperatures (As and Af) such that the shape memory alloy exhibits stress induced martensite up to a temperature Md, greater than Af and within the range of ambient temperatures the support members are exposed. For example, nickel titanium having an atomic ratio of 51.2% Ni and 48.8% Ti exhibits an Af of approximately −20° C.; nickel titanium having an atomic ratio of 50% Ni to 50% Ti exhibits an Af of approximately 100° C. [Melzer A, Pelton A. Superelastic Shape-Memory Technology of Nitinol in Medicine. Min Invas Ther & Allied Technol. 2000: 9(2) 59–60]. Such materials are able to withstand strain as high as 10% without plastically deforming. As such, these superelastic materials are capable of elastically exerting force upon deflection. Materials other than superelastic shape memory alloys may be used as support members provided they can be elastically deformed within the temperature, stress, and strain parameters required to maximize the elastic restoring force thereby enabling the shoe sole to exert force against the foot upon deflection. Such materials include other shape memory alloys, spring stainless steel 17-7, Elgiloy, superelastic polymers, etc.

The embodiments of the invention provide superelastic support members in the soles of shoes that exert force against the foot upon deflection. These superelastic support members produce a cushioning to ease the localized pounding effects, on the foot, of landing against hard surfaces while walking, running, or jumping. They also exert a directional force on the foot to enhance the vertical leap when jumping, the lateral agility when cutting or dodging, and the forward stride when running or walking. The embodiments of the invention also provide superelastic support members to correct pronation, supenation, or other foot position abnormality. To accomplish this, the superelastic support members may be selected and distributed to produce a predefined stiffness profile throughout the sole of the foot and/or bias the foot inward, outward, backward, forward, or other pattern that maximizes the utility of the specific shoe sole.

The embodiments of the invention also provide superelastic support members along the ankle, the heel, the toe, and/or the arch of the foot to prevent twisting the ankle, which causes injury to the foot. The embodiments of the invention also provide ankle braces, elbow braces, shoulder supports, wrist supports, and knee braces which incorporate superelastic support members to reinforce the ankle, wrist, elbow, shoulder, or knee and prevent abrupt twisting or separation of the joints, which may result in injury.

Figures 1A, 1B:
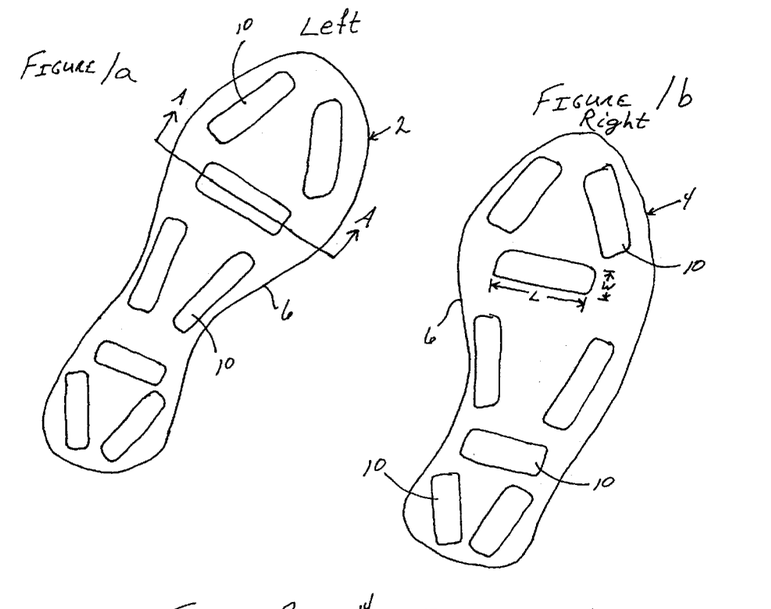

FIGS. 1a and b show the soles, 2 and 4, of a left shoe 8 and a right shoe 8, respectively. The soles 2 or 4 incorporate superelastic support members 10 distributed throughout the body of the sole. This distribution and the characteristics of each superelastic support member determines the purpose for the shoe sole and the amount of force the sole is capable of exerting against the foot. The superelastic support members have at least one width, W, and at least one length, L, configured to produce the desired stiffness and force profile. The sole material 6 encompassing the superelastic support members is configured to include compartments that restrain the support members and maintain the desired elasticity and stiffness profile of the sole. The shoe sole may be fabricated from phylon, TPU (thermoplastic urethane), TPVR (thermopolyvinyl resin) TPR (thermoplastic rubber), EVA, polyurethane, napos, PEBAX™, carbonized rubber, other conventional sole materials, silicone, elastomer, other polymer, or a combination of these materials. The shoe sole maintains the position of the superelastic support members and permit the desired deflection of the superelastic support members without degrading.

Figures 2A, 2B:
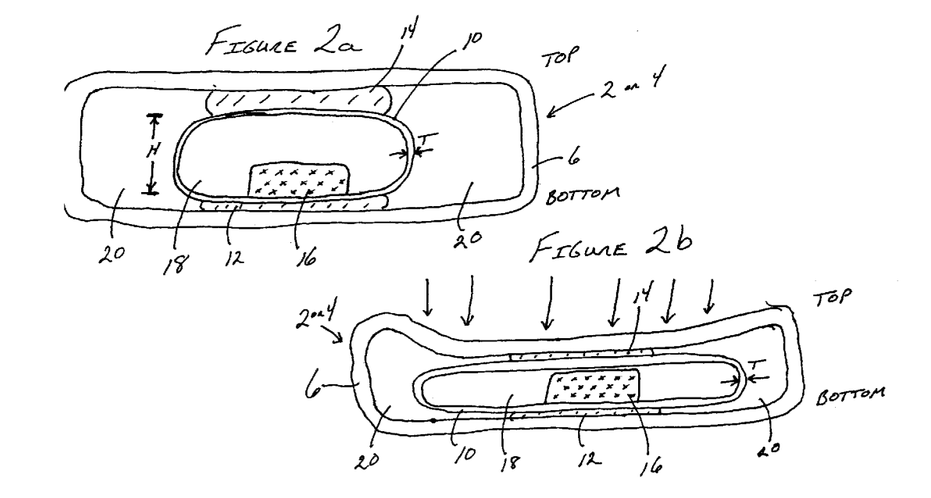
FIG. 2a shows a cross-sectional view of the sole of FIG. 1a taken along line A—A.
FIG. 2b shows the cross-sectional view of FIG. 2a with an external force exerted against the top of the shoe sole, as indicated by arrows.

FIG. 2a shows a cross-sectional view of the sole in FIG. 1a taken along line A—A. The superelastic support member 10 has a wall thickness, T, and a height, H, which influence the stiffness and force profile of the sole, along with the width, W, and length, L. The sole, 2 or 4, incorporates at least one compartment 20 configured to house and permit deflection of the superelastic support member 10, as shown in FIG. 2b. The support member 10 is secured to the bottom 12 and top 14 of the shoe sole, 2 or 4, by applying flexible adhesives between the bond joints, restraining in compartments adapted to maintain the position of the support member, sewing, or using rivets or other mechanical attachment means. Alternatively, the bottom and top of the support members may be laminated between layers of or otherwise embedded in the sole material 6. The support members may incorporate an interior cavity 18, which permits the necessary deflection, and a stop 16 attached to the top or bottom of the support member designed to restrict deflection of the support members. The stop 16 prevents excess deflection of the support members, which could cause the strain to exceed the approximate 10% limit that most superelastic materials are able to withstand without permanent deformation. Excess strain may result in plastic deformation or failure of the support member, rendering the sole defective. The stops 16 may be fabricated from silicone, urethane, an elastomer, or other elastic polymer.

Figure 3A:
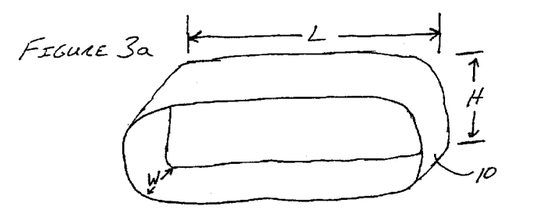
FIGS. 3a to i show configurations of superelastic support members.

FIGS. 3*a* to *i* show representative superelastic support member embodiments of the invention. As shown in FIGS. 3*a* and *d*, the support member 10 may be fabricated from a complete tube having an oval, circular, rectangular, square, trapezoidal, or other cross-sectional geometry. The support members 10 may be fabricated by extruding, press-forging, rotary forging, bar rolling, sheet rolling, cold drawing, cold rolling, using multiple cold-working and annealing steps, or otherwise forming into the desired tube. Then the support members 10 must be cut into the desired width. Conventional abrasive sawing, waterjet cutting, laser cutting, EDM machining, photochemical etching, or other etching techniques may be employed to cut the support members from the raw material. After cutting the desired pattern of the support members, the support members are formed into the desired shape, heated, for example, between 300° C. and 550° C., and allowed to cool in the preformed geometry to set the shape of the support members.

Figures 3B, 3C:
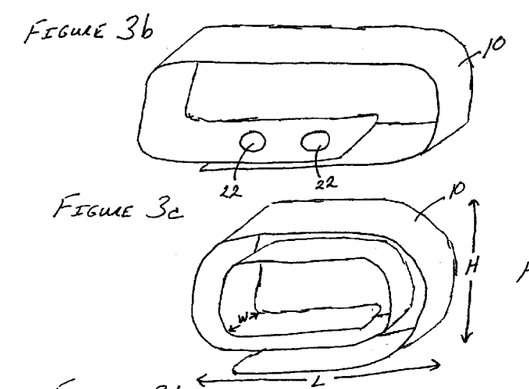
Figure 3D:
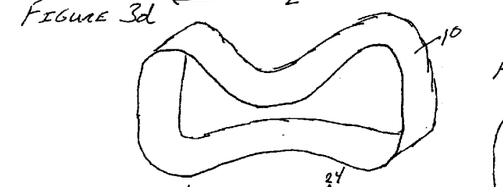

Alternatively, the support members 10 may be fabricated as sheets having the desired width, W, and wall thickness, T, and thermally shaped into the desired cross-sectional geometry. As shown in FIGS. 3*b*, *e*, and *i*, opposite ends of the thermally formed support member may be secured by using rivets 22, applying adhesives, welding, soldering, mechanically engaging 28 into 26, utilizing another bonding means, or a combination of these bonding methods. As shown in FIGS. 3*c*, *f*, and *g*, opposite ends of the thermally formed support member may be free-floating to permit increased deflection. This results in a phase shift in the reversion from a deflected position to the expanded baseline orientation; this produces a time delay between the deflection and the return towards the preformed configuration. This time delay may be tailored to enhance the running or jumping action by applying the force against the foot at the desired instant to maximize the effect. As shown in FIG. 3*h*, the support member may be fabricated with internal supports 30 to increase the stiffness and provide additional reinforcement along the length of the support member 10.

Figures 3E, 3F:
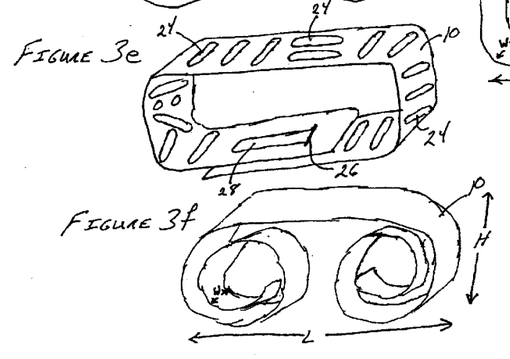
Figure 3G:
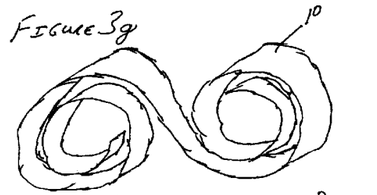
Figure 3H:
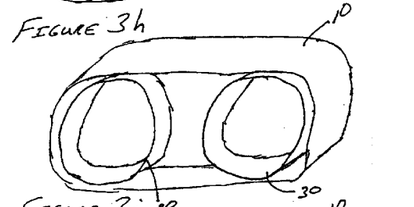
Figure 3I:
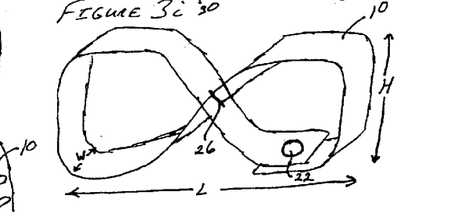

As shown in FIG. 3*e*, slots 24, holes, or other cut-away areas may be incorporated in the support member design to tailor the stiffness profile of the support member 10. Cutting processes described above may be used to fabricate the slots, holes, or cut-away regions in the desired pattern to taper the stiffness along the support member, focus the stiffness of the support members at the edges, reinforce the center of the support member, or otherwise customize the stiffness profile.

Figures 4A, 4B:
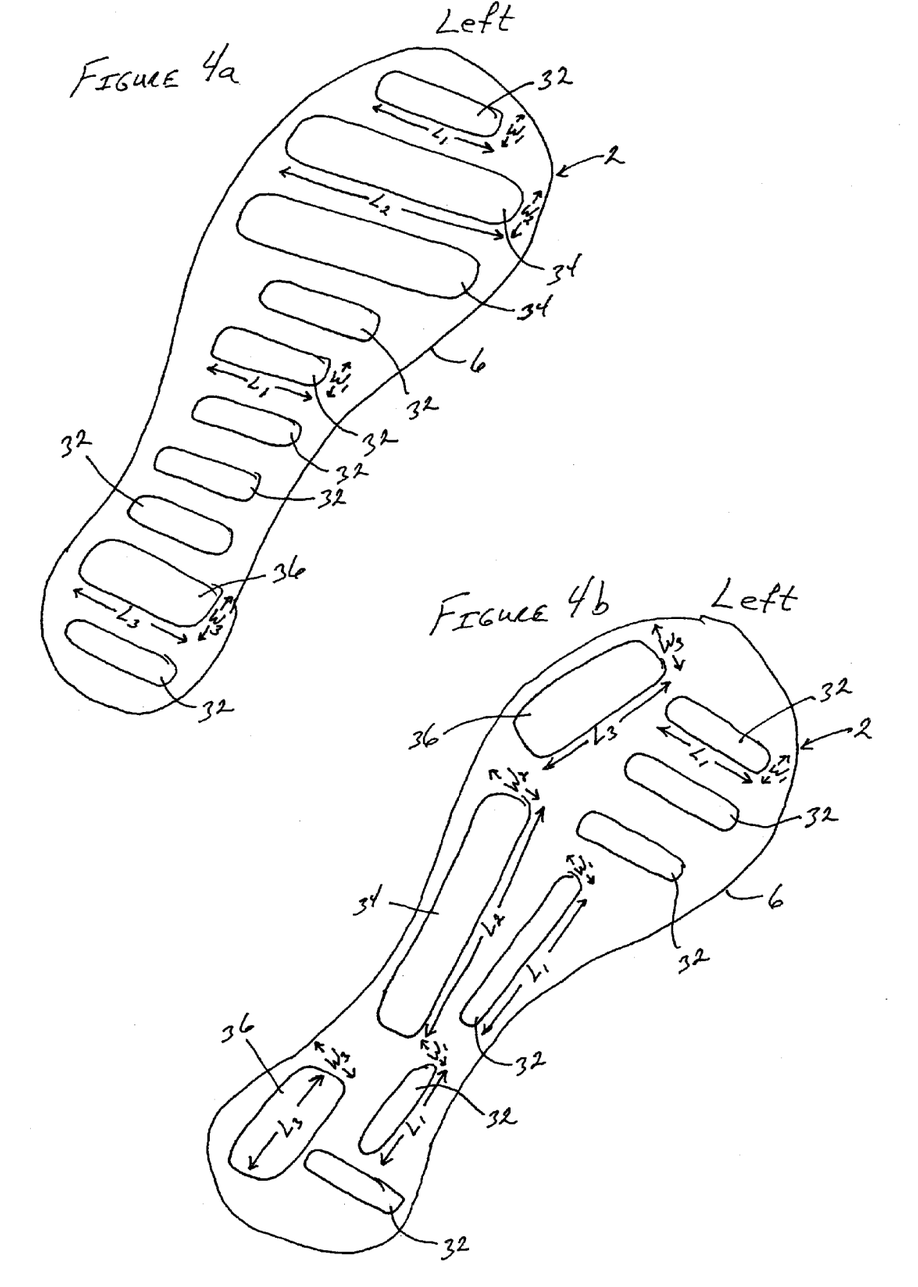
FIGS. 4a to f show top views of various shoe sole configurations that incorporate superelastic members.

As shown in FIG. 4*a*, various superelastic support member configurations, each having specific stiffness and elastic characteristics, may be incorporated into the shoe sole 2. The shoe sole in FIG. 4*a* incorporates three types of support member configurations designed to exert the desired force profile against the foot. In this sole embodiment, the most stiff support members 34 are located at the balls of the foot, less stiff support members 36 are located at the heel, and the least stiff support members 32 along the arch of the foot and at the distal end of the foot. This is desired configuration for running and jumping because the largest upward force is associated with deflection of the sole at the balls of the foot. The support members located at the heel are primarily configured to provide cushioning, but may also direct the foot forward urging the balls of the foot against the ground surface to impart the desired running form. This prevents unwanted running forms such as hitting the surface flat-footed, which can cause injury. As discussed previously, various superelastic support member parameters may be tailored for the desired stiffness profile; these include length, width, wall thickness, height, material, and geometry.

FIG. 4*b* shows an alternative distribution of superelastic support members for the left shoe sole. This distribution of superelastic support members corrects pronation of the foot by placing stiffer superelastic support members 36 along the outside edge of the sole and the least stiff support members 32 along the inside region of the sole. This directs the foot inward to correct for the natural tendency of pronated feet to deflect outwards. FIG. 4*d* shows another superelastic support member distribution designed to address pronation. In this case, the stiffness of the outer support members 38 is not only larger than the inside support members 32 but is tapered to further urge the foot inward and correct pronation.

Figure 4C:
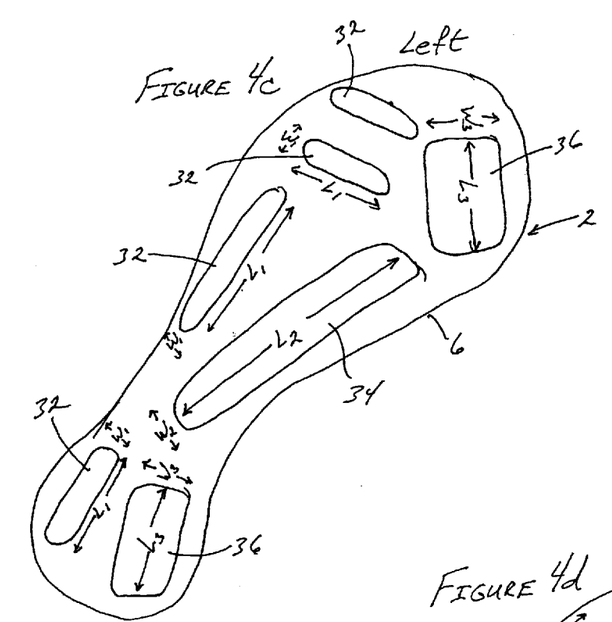
Figure 4D:
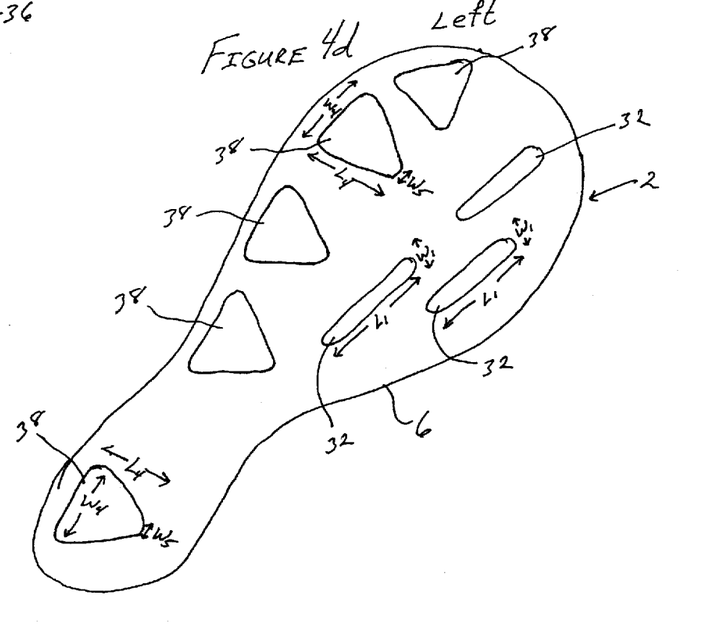
Figure 4E:
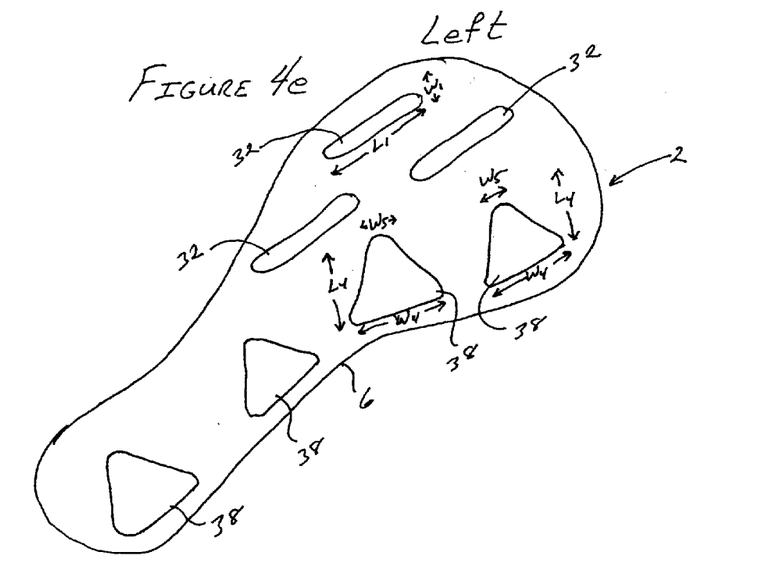
Figure 4F:
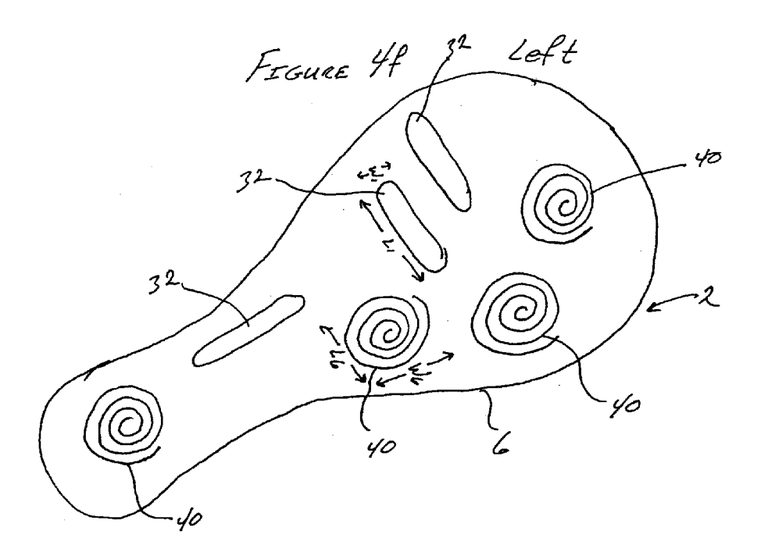

FIG. 4*c* shows a superelastic support member distribution configured to address supenation by positioning stiffer support members 36 along the inside region of the sole and the least stiff support members 32 along the outside region of the sole. FIG. 4*e* shows another superelastic support member distribution configured to address supenation by urging the foot outward. This distribution uses inner support members 38 that are stiffer than the outer support members 32 and are tapered to further direct the foot outward and correct supenation. FIG. 4*f* shows another superelastic support member distribution configured to address supenation; coiled inner support members 40 are stiffer than the outer support members 32 and direct the foot outward.

Figure 5A:
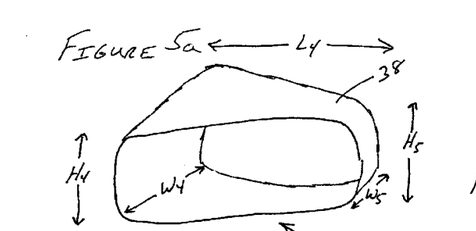
FIGS. 5a to g show configurations of superelastic support members.
Figure 5B:
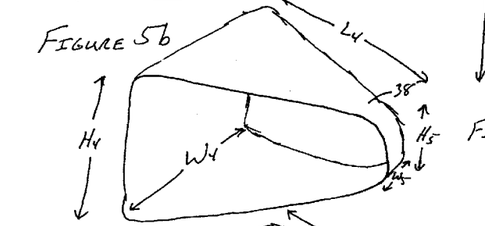
Figure 5C:
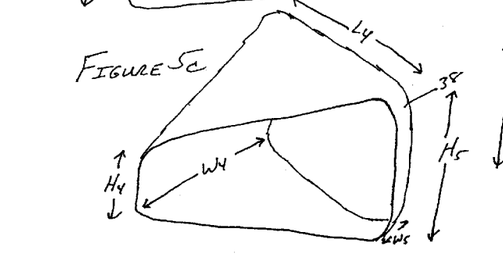
Figure 5D:
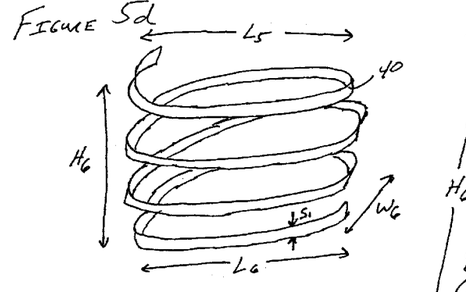
Figure 5E:
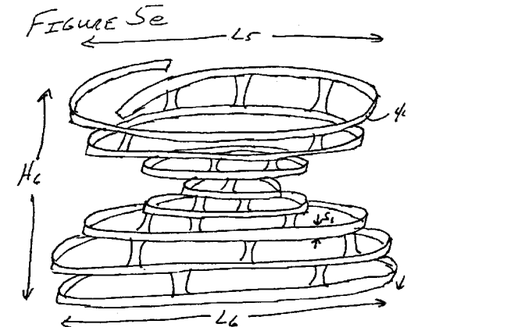
Figure 5F:
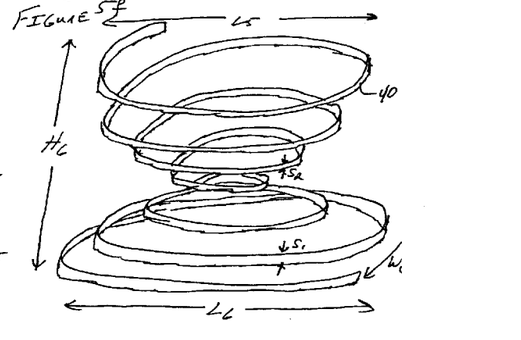
Figure 5G:
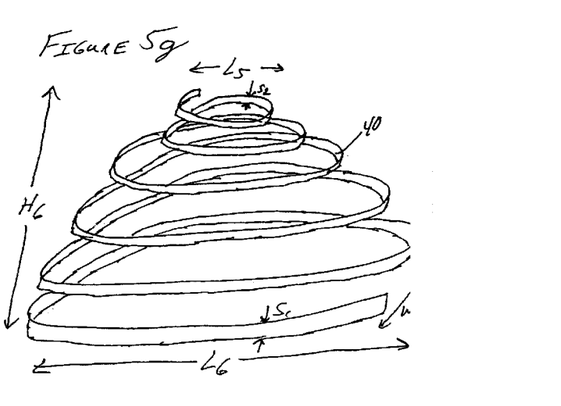

FIGS. 5*a* to *c* show a variety of tapered support member configurations 38. In FIG. 5*a*, W4 is larger than W5 and H4 equals H5. In FIG. 5*b*, W4 is larger than W5 and H4 is larger than H5. In FIG. 5*c*, W4 is larger than W5 and H4 is smaller than H5. The change in widths imparts a stiffness profile along the length L4 of the superelastic support member. The change in height also affects the stiffness but also directs the foot away from the side of the support member having a larger height. This may be used to enhance the treatment of pronation or supenation previously described. The change in heights may also be used to better encompass the foot and provide increased support of the sides of the foot. By positioning the support members such that the side with the largest height abuts the side of the shoe sole, the foot seats in the middle region of the sole and is better supported by the sides. This may help prevent rolling the foot, which may cause ankle injuries.

FIGS. 5*d* to *g* show a variety of coiled superelastic support member 40 configurations. The wall thickness, T, strand width, S1 or S2, height, H6, width, W6, and length, L5 and L6, are chosen to specify the stiffness profile along the shoe sole, as previously described.

Figure 6A:
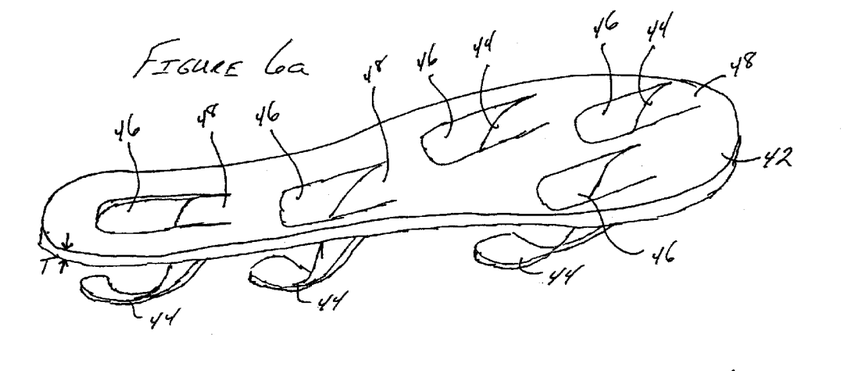
FIGS. 6a to c show configurations of superelastic support members.
Figure 6B:
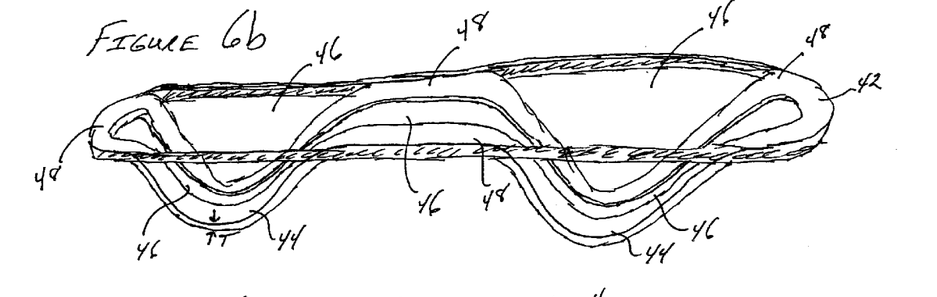
Figure 6C:
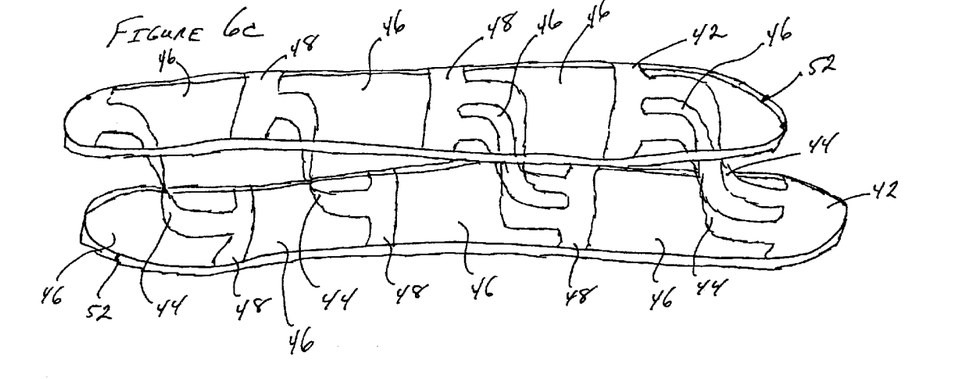

FIGS. 6*a* to *c* show superelastic support members 42 fabricated with the individual supports 44 integrated together 48 and 52. These support members 42 may be fabricated from a sheet of superelastic material cut 46 and thermally formed into the desired pattern. By integrating the individual supports 44, manufacturing of the shoe sole is facilitated by embedding the integrated unit in the sole material 6 as opposed to having to individually form and position discrete support members.

Figure 7A:
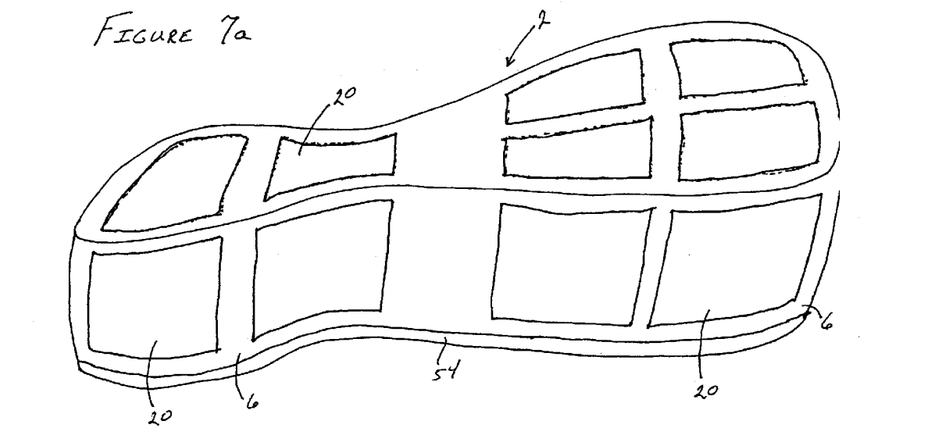
FIGS. 7a and b show shoe soles that incorporate compartments into which superelastic support members may be positioned and secured.
Figure 7B:
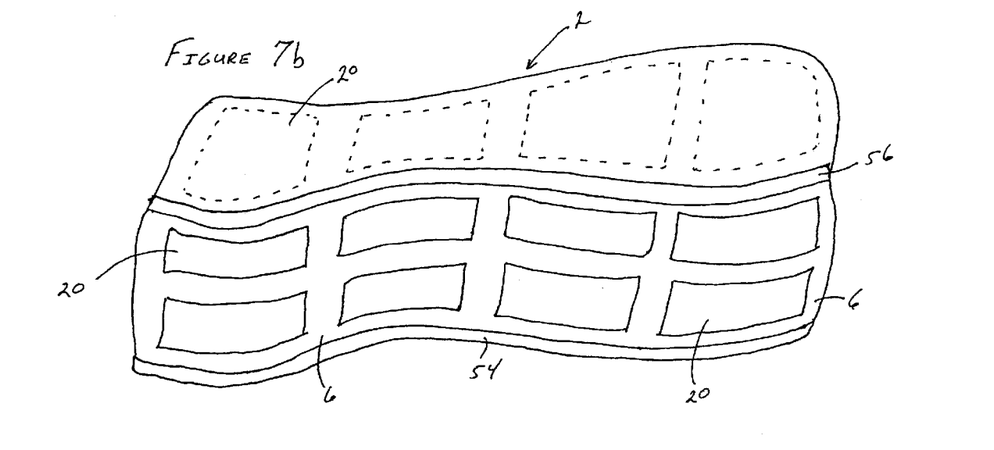

FIGS. 7a and b show a shoe sole inherently incorporating compartments 20 designed to house the individual support members (not shown). One row of compartments may be used as shown in FIG. 7a; alternatively two or more rows of compartments may be used as shown in FIG. 7b. The number of rows and location of the compartments depends on the desired stiffness and force profile to address the specific shoe market. In addition, the sole of the shoe may be fabricated such that the support members may be removed, re-distributed, or replaced without having to purchase a new pair of shoes. This enables varying the impact of the shoe sole to address different athletic requirements (e.g. court shoes versus running shoes) or therapeutic regimens (e.g. gradually correct pronation, supernation, or other abnormality by gradually changing the degree of inward or outward biasing). The insole 54 or 56 of the shoe may be fabricated as removable so that access into the compartments 20 enables removing and placing the support members into the various compartments. The insole 54 or 56 may be fabricated as removable by incorporating a Velcro type attachment between the in-sole and sole of the shoe. Other temporary attachment means may alternatively be used.

Figure 8A:
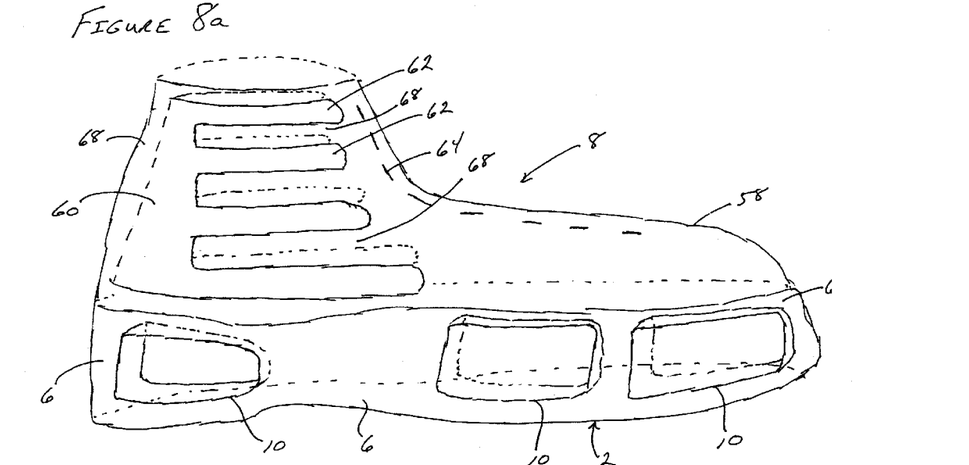
FIGS. 8a and b show shoes that incorporate superelastic support members in the soles and throughout the body of the shoe.
Figure 8B:
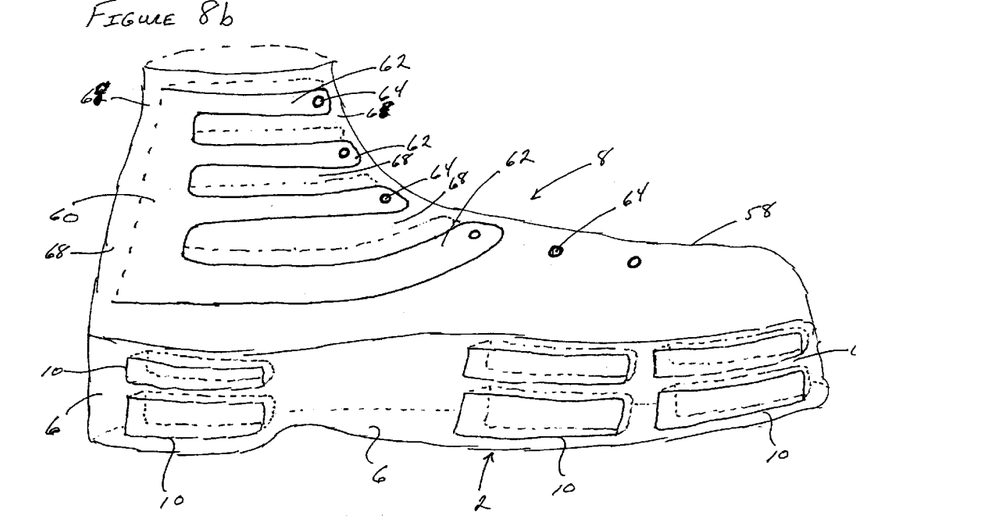

FIGS. 8a and b show superelastic support members incorporated in the ankle region of the shoe. The extensions 62 of the support member ribcage may terminate prior to the shoelace holes, as shown in FIG. 8a, or may encompass the shoelace holes 64, as shown in FIG. 8b. By encompassing the shoelace holes 64 at the ends of the superelastic support member extensions, the support members reinforce the ankle completely once the shoelaces are tied tightly. These support members limit the motion of the foot 58 significantly more than merely increasing the height of the ankle region of the shoe. As such these support members better restrict rotation or twisting of the ankle thereby preventing ankle injuries commonly observed with court shoes and hightop shoes.

Alternatively, shoelace holes may be eliminated from the shoe and the extensions 62 of the support member ribcage may be used to keep the shoe tight around the foot without having to tie laces. The superelastic extensions 62 permit deflection while inserting the foot into the shoe. Once the external force urging the extensions 62 outward is removed, the extensions 62 return towards their preformed configuration around the foot to reinforce the foot and maintain the position of the foot without requiring additional scaffolding, such as tying laces.

Figure 9A:
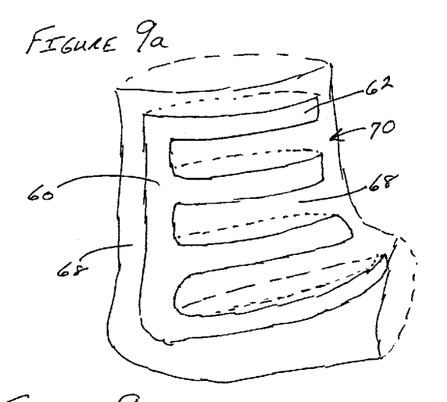
FIG. 9a shows an ankle brace that incorporates at least one superelastic support member.

As opposed to incorporating the superelastic support members in the ankle region of the shoe, ankle braces 70 incorporating superelastic support members may be used. As shown in FIG. 9a, the ankle brace 70 (or other anatomic brace) may incorporate a support member structure 60 embedded in a covering 68. The covering 68 or shoe material (discussed above) may be fabricated from neoprene, fabric mesh, LYCRA™, SPANDEX™, leather, rubber, PEBAX™, nylon, polyester, other cushioning material typically used in ankle braces and demonstrating excellent elasticity, or a combination of these materials. The support members may be inserted between layers of the covering material; the layers of the covering may be bonded together using adhesives, ultrasonically welding, thermally welding, radiofrequency welding or other bonding process.

Figure 9B:
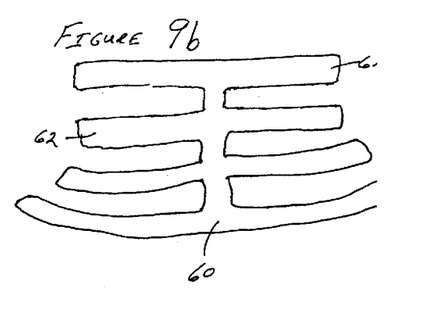

The support member structure in FIG. 9a is a ribcage incorporating a primary section oriented axially along the ankle region and multiple secondary sections 62 extending transversally from the primary section. The secondary sections 62 extend partially or completely around the ankle (or other anatomic structure). As shown in FIG. 9b, the support member structure 60 may be fabricated from a flat sheet of superelastic material. Opposite ends of the secondary sections 62 may be bonded together by welding (using lasers, electron beam, or other suitable process), soldering, using adhesives, or utilizing mechanical securing means to cause the secondary sections to extend completely around the ankle. Alternatively, the secondary sections 62 may be thermally formed to extend partially or completely around the ankle without bonding the opposite ends. Another way to fabricate superelastic support member structures 60 having secondary sections extending completely around the ankle is to fabricate the support member pattern from tube stock or superelastic material having a 3-dimensional geometry.

Figure 9C:
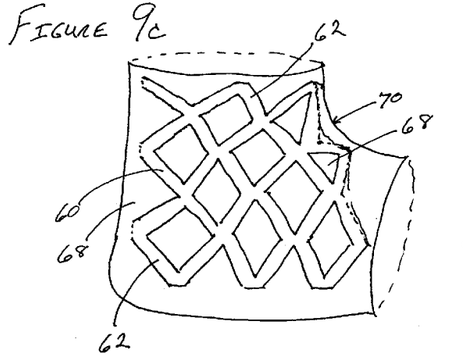
FIGS. 9c to d show alternative ankle brace embodiments that include at least one superelastic support member.
Figure 9D:
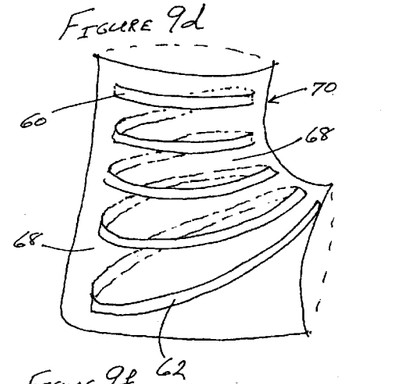
Figure 9E:
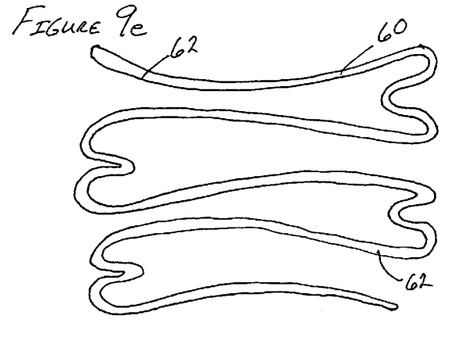
FIG. 9e shows an alternative superelastic support member embodiment for an ankle brace.

FIGS. 9c and d show alternative ankle brace embodiments in which the superelastic support member structures extend completely around the ankle region of the brace. The support member structure embodiments shown in FIGS. 9c and d are expandable so as to enable increased compression force of the brace against the ankle; this further limits rotation, rolling, or twisting of the ankle. The support member structure of FIG. 9c is a mesh structure, which enables enlargement of the mesh cells in response to an external force. Alternative mesh structure embodiments, not shown, may be substituted for the support member ribcage in FIG. 9c. The support member structure in FIG. 9d is a helical coil. This permits enlargement of the ankle brace in response to an external force and tends to return toward the resting, thermally formed configuration. FIG. 9e shows an alternative support member structure for an ankle brace.

Figure 9F:
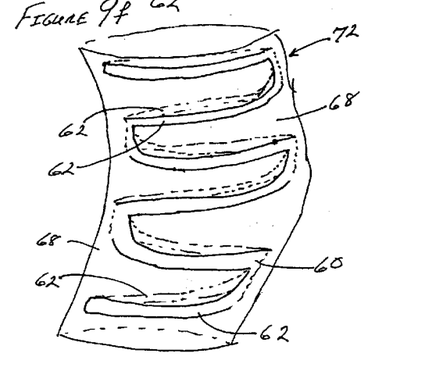
FIG. 9f shows a knee brace that incorporates at least one superelastic support member.

The support member structures previously described for the ankle braces may additionally be utilized for knee, wrist, shoulder, or elbow braces. FIG. 9f shows a knee brace 72 that incorporates a support member structure 60 that reinforces the knee joint. These support member structures 60 aid the brace in preventing over-rotating, excess twisting, unwanted rolling or separation of the tissues at the joint. Cut-outs around the knee cap (or other anatomic feature, depending on the intended use) or tapered extensions of the support member structure may be incorporated in the brace design by ensuring material (support member structure and/or covering) is removed or the stiffness of the material is reduced in these regions.

Alternatively, these support member structures may be used in braces that reinforce the ribs, shin, or other bone to prevent localized stressing that may result in fracture, bruising, or other injury. Alternatively, these support member structures may be incorporated in braces intended to reinforce sprained joints, fractured bones, or other injuries in which the joint or anatomic region must be reinforced or stabilized so they heal properly. The ability to thermally shape the support member structures to any form enables customizing the support member structures to the patients anatomy. In addition, these support member structures may be used in braces that reinforce the sternum or ribs and apply continuous force against the sternum or ribs after open chest surgery involving a medium sternotomy, thoracotomy, or thoracostomy. This facilitates and quickens healing of the sternum or ribs after surgery.

Figure 10A:
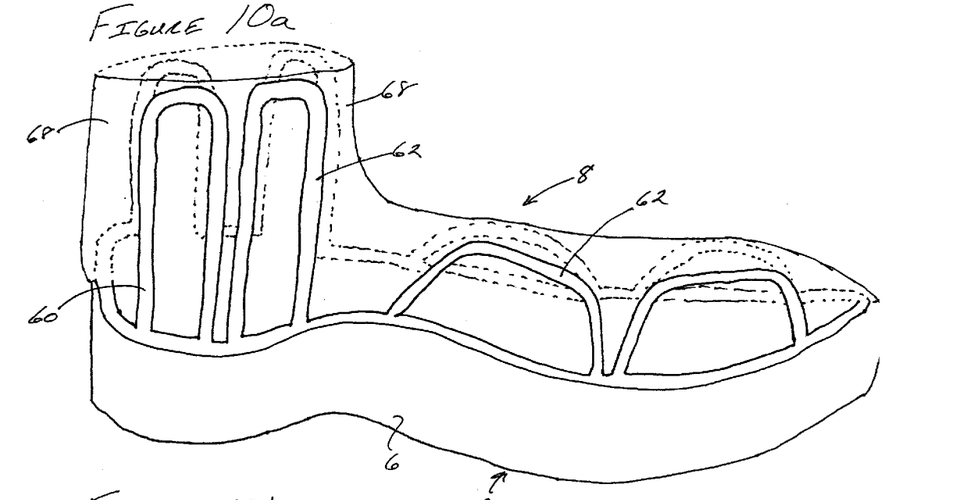
FIG. 10a shows a shoe that incorporates a superelastic support member throughout the body of the shoe.
Figure 10B:
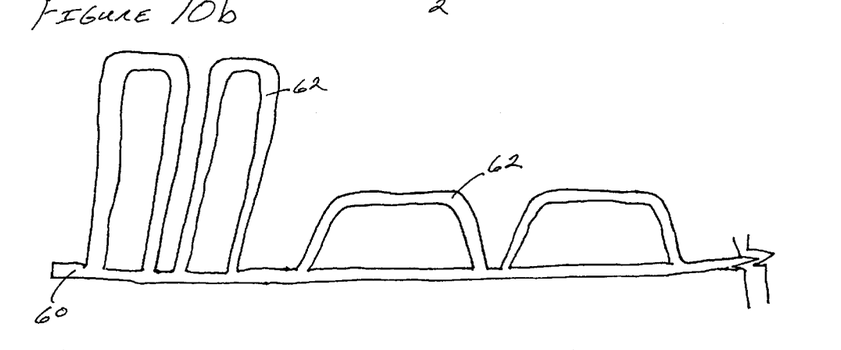
Figure 11:
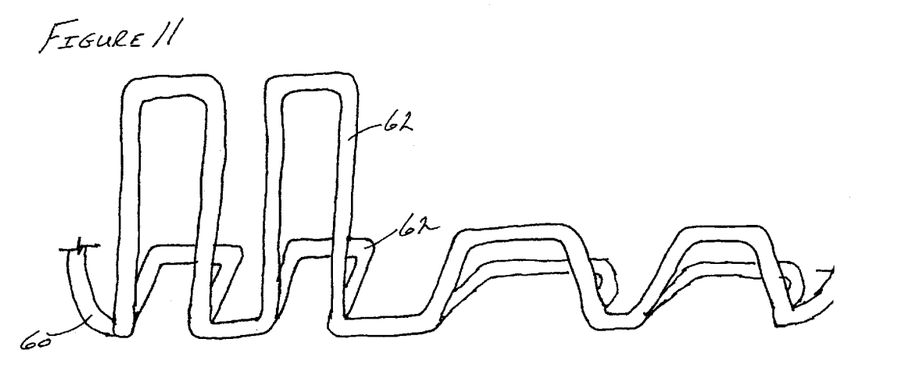
FIG. 11 shows an alternative superelastic support member embodiment for the body of a shoe.
Figure 12:
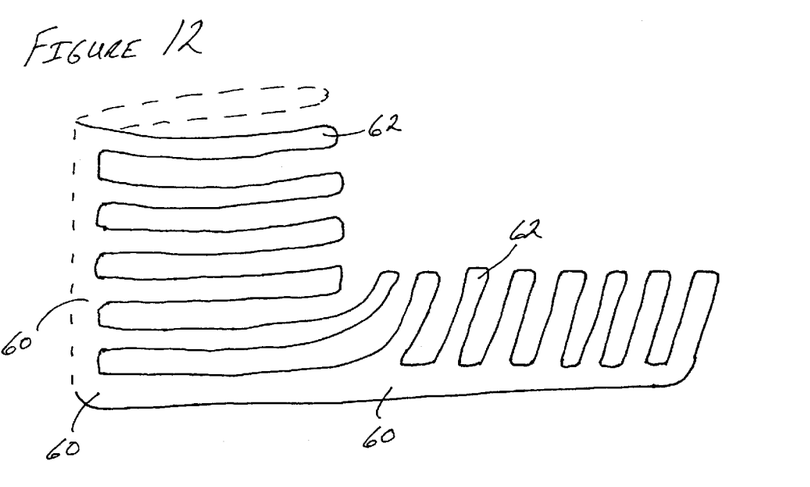
FIG. 12 shows another superelastic support member embodiment for the body of a shoe.

For certain situations, the support member structure 60 is designed to reinforce the body and/or toe region of the foot, in addition to the ankle region as previously described. FIG. 10a shows a support member structure 60 that incorporates extensions 62 located at the ankle region of the shoe and along the body and/or toe region of the foot. The length of the extensions 62, especially those located at the body and/or toe region of the foot depend on the required reinforcement parameters. These support member structures better prevent rolling of the foot or separation of the ankle from the body of the foot than solely reinforcing the ankle, as previously described. FIG. 10b shows the support member structure of FIG. 10a in a flattened configuration. This support member structure may be fabricated from a sheet of superelastic material cut into the desired pattern of primary sections and extensions, and thermally shaped into the desired configuration. Opposite ends of the support member structure may or may not be bonded together using attachment means previously described. FIG. 11 shows an alternative support member structure 60 that reinforces the bottom of the foot along with the sides and top of the foot. In this configuration, support member extensions 62 are located at the ankle, the body and toe region, the heel, the arch, and the ball of the foot. This configuration reinforces the entire foot as opposed to a single region of the foot. FIG. 12 shows another support member structure 60 that reinforces the ankle region along with the body and toe region of the foot. In this embodiment, the ankle region of the support member structure is attached to the body and toe region such that the support member structure inhibits excess bending, twisting, rolling, or rotation of the ankle relative to the body or toe region of the foot; this further prevents ankle injuries resulting from overextending the ankle joint.

Shoes incorporating support member structures 60 that reinforce the ankle, body, and toe region of the foot may be utilized in activities such as race car driving. Because superelastic materials may be fabricated thin yet remain strong, light, and flexible, they may function as shields capable of repelling projectiles, such as pieces of carbon fiber encountered during automobile wrecks. To address such applications, the support member structures must prevent localized over-stressing of the foot, which may cause injury. These support member structures 60 withstand extreme heat (>100° C.) without melting, deforming, or breaking down, are very light, and may be fabricated with comparably thin cross-sections while still maintaining the ability to reinforce the foot and prevent localized overstressing. As such, they are applicable in shoes that are worn during athletics, work, or other events in which the possibility of over-stressing the foot warrants reinforcements to prevent injury, even when exposed to extreme heat.

The properties of the superelastic support members or structures described above may be varied to address applications in which the stiffness or elasticity needs to be varied accordingly. The composition of the superelastic material may be chosen to select the temperature range in which the support members or structures exhibit stress-induced martensite. As such, the amount of austenite, and stress-induced martensite characteristics throughout a specific temperature range may be chosen to specify the degree of deflection and amount of force exerted by the superelastic support member once deflected. For example, the superelastic properties of the material may be chosen so as exercise (or other activity) increases, the associated temperature increase induces a change in the superelastic properties of the superelastic support member or structure to provide, for example, increased rigidity and/or elasticity of the material.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims of the invention.

We claim as our invention:

1. An orthopedic device for reinforcing an anatomic joint of a body comprising:

a structure fabricated from at least one superelastic member incorporating at least one radial component extending completely around said anatomic joint, and at least one axial component extending from above said anatomic joint to below said anatomic joint;

a covering encapsulating said structure;

wherein said superelastic member withstands a maximum strain of about 10 percent without plastically deforming; and said structure deflects from a first configuration to a second, stressed configuration in response to an external force and completely returns to said first configuration upon removing said external force.

2. The device of claim 1, wherein said covering comprises the ankle region of a shoe;

the covering is bonded to the sole of said shoe; and said structure is embedded between layers of said covering.

3. The device of claim 1, wherein said structure and covering comprise a joint brace.

4. The device of claim 1, wherein said radial and axial components comprise a single component.

5. The device of claim 1, wherein said radial and axial components comprise intersecting components.

6. The device of claim 1, wherein said at least one superelastic member extends around said anatomic joint multiple times.

7. The device of claim 1, wherein said at least one superelastic member comprises nickel titanium.

8. The device of claim 1, wherein said structure defines an opening with a central axis, and said structure deflects about an axis not parallel to said central axis in response to an external force, said structure returns toward its preformed configuration when the external force is reduced or removed.

9. The device of claim 1, wherein said structure defines an opening with a central axis, and said structure expands about said central axis in response to an external force for placement around said anatomic joint, said structure returns toward its preformed configuration when the external force is reduced or removed.

* * * * *